United States Patent [19]

Terao et al.

[11] Patent Number: 4,489,096
[45] Date of Patent: Dec. 18, 1984

[54] QUINONE COMPOUNDS, THEIR PRODUCTION AND USE

[75] Inventors: Shinji Terao, Toyonaka; Yoshitaka Maki, Kyoto, both of Japan

[73] Assignee: Takeda Chemical Industries, Ltd., Osaka, Japan

[21] Appl. No.: 511,083

[22] Filed: Jul. 5, 1983

[30] Foreign Application Priority Data

Jul. 9, 1982 [JP]  Japan ................... 57-120194

[51] Int. Cl.³ .................. A61K 31/2; A61K 31/275; C07C 50/00; C07C 50/14
[52] U.S. Cl. .................. 424/317; 424/300; 424/305; 424/308; 424/311; 424/316; 424/318; 424/320; 424/323; 424/324; 424/331; 424/333; 260/396 R; 260/396 N
[58] Field of Search ............. 260/396 R, 396 N; 424/317, 305, 320, 323, 333, 300, 308, 331, 311, 324, 316, 318

[56] References Cited

U.S. PATENT DOCUMENTS

| | | | |
|---|---|---|---|
| 3,346,595 | 10/1967 | Folkers et al. | 260/396 R |
| 3,957,836 | 5/1976 | Morimoto et al. | 424/316 |
| 4,199,531 | 4/1980 | Terao et al. | 260/396 R |
| 4,393,075 | 7/1983 | Terao et al. | 424/317 |

OTHER PUBLICATIONS

*J. Chem. Soc. Perkin Trans. I,* Shiraishi et al., (7), 1591-9, 1982.

*Primary Examiner*—Richard Raymond
*Assistant Examiner*—Raymond K. Covington
*Attorney, Agent, or Firm*—Wenderoth, Lind & Ponack

[57] ABSTRACT

New quinone compounds of the formula:

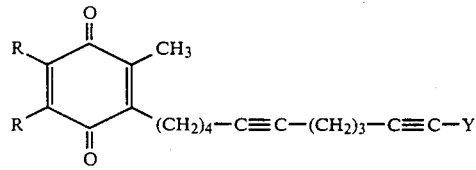

wherein
R is methyl or methoxy and
Y is formyl, carboxyl, an alkoxycarbonyl having 2 to 5 carbon atoms, carbamoyl, a mono- or di- alkylcarbamoyl whose alkyl moiety has 1 to 4 carbon atoms or carbamoyloxymethyl, or their hydroquinone-form compounds, or pharmaceutically acceptable salts thereof, have useful physiological activities such as antiasthmatic and antiallergic activities.

9 Claims, No Drawings

QUINONE COMPOUNDS, THEIR PRODUCTION AND USE

This invention relates to novel quinone compounds useful as drugs or intermediates therefor.

More particularly, this invention relates to: a quinone compound of the formula:

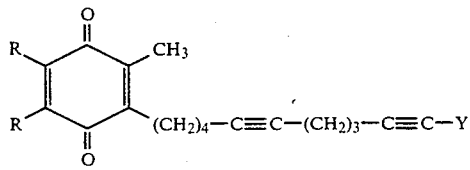

wherein
R is methyl or methoxy and
Y is formyl, carboxyl, an alkoxycarbonyl having 2 to 5 carbon atoms, carbamoyl, a mono- or dialkylcarbamoyl whose alkyl moiety has 1 to 4 carbon atoms, or carbamoyloxymethyl, or its hydroquinone-form compound, or a pharmaceutically acceptable salt thereof.

The hydroquinone-form compound of the above quinone compound (Ia) is represented by the formula:

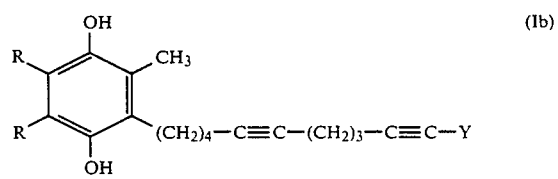

wherein R and Y are as defined above.

Referring to the above formulas (Ia) and (Ib), the alkoxycarbonyl having 2 to 5 carbon atoms represented by Y includes methoxycarbonyl, ethoxycarbonyl, propoxycarbonyl, isopropoxycarbonyl, butoxycarbonyl, isobutoxycarbonyl and tert-butoxycarbonyl, among others. The mono- or dialkylcarbamoyl whose alkyl moiety has 1 to 4 carbon atoms is, for example, methylcarbamoyl, ethylcarbamoyl, propylcarbamoyl, isopropylcarbamoyl, dimethylcarbamoyl or diethylcarbamoyl.

Among the compounds provided by the present invention, those compounds in which Y is a carboxyl group are generally preferred from the viewpoint of achieving the object of the present invention. Furthermore, a methyl group is a preferred species of R.

Among the compounds of the present invention, the compounds (Ia) and (Ib) wherein Y is carboxyl may form a pharmaceutically acceptable salt. As examples of pharmaceutically acceptable salts, there may be mentioned alkali metal salts such as sodium salts, potassium salts, etc.

The compounds (Ia) and (Ib) of the present invention can be produced, for example, by subjecting a compound of the formula:

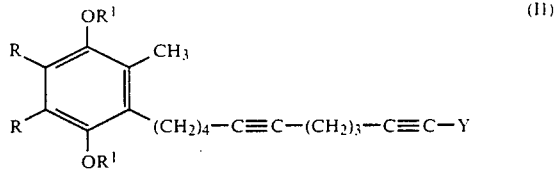

wherein R and Y are as defined above, and $R^1$ is an alkyl having 1 to 3 carbon atoms, benzyl, methoxymethyl or tetrahydropyranyl, to deprotection. That is, the compound (Ia) can be obtained by subjecting the compound (II) wherein $R^1$ is an alkyl having 1 to 3 carbon atoms or benzyl to oxidative dealkylation, whereby deprotection and oxidation of the benzene ring take place, while the compound (Ib) can be obtained by subjecting the compound (II) wherein $R^1$ is methoxymethyl or tetrahydropyranyl to solvolysis, whereby deprotection occurs.

The oxidative dealkylation of the compound (II) wherein $R^1$ is an alkyl having 1 to 3 carbon atoms or benzyl is carried out using a divalent silver compound (e.g. AgO) or a cerium compound [e.g. $Ce(NH_4)_2(NO_3)_6$], for instance. Thus, for example, the compound (II) is reacted with AgO-nitric acid in water or an aqueous organic solvent (e.g. dioxane, acetonitrile) or is reacted with AgO or ammonium cerium (IV) nitrate in the presence of pyridine-2,6-dicarboxylic acid, pyridine-2,6-dicarboxylic acid N-oxide or pyridine-2,4,6-tricarboxylic acid in a solvent such as mentioned above. The amount of oxidizing agent is usually 2 to 3 moles per mole of the compound (II). The reaction temperature may generally be about $-10°$ C. to about $+30°$ C., preferably about $-5°$ C. to about $+10°$ C. The reaction time is usually 30 minutes to one hour.

The solvolysis of the compound (II) wherein $R^1$ is methoxymethyl or tetrahydropyranyl is carried out by contacting the compound (II) with an acid such as a mineral acid (hydrochloric acid, sulfuric acid, etc.), an organic sulfuric acid (methane sulfonic acid, p-toluene sulfonic acid, camphor sulfonic acid, etc.) in the presence of an organic solvent such as methanol, ethanol, dioxane, acetonitrile, or a mixture of water and one of these solvents. The amount of acid is usually 0.005 to 0.1 mole per mole of compound (II). The reaction temperature is usually in the range of from 0° C. to 60° C., the reaction time is usually 1 to 5 hours.

Among the compounds (Ia), a compound of the formula:

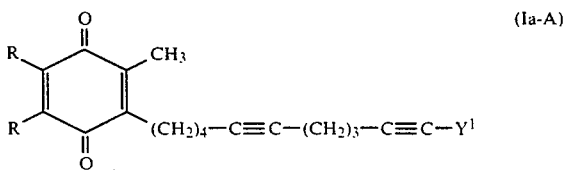

wherein $Y^1$ is formyl or carboxyl can also be produced, for example, by oxidizing a compound of the formula:

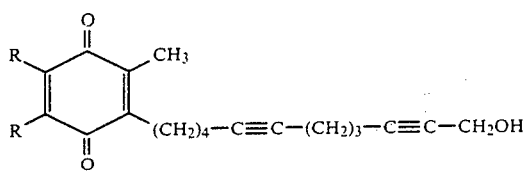

(III)

wherein R is as defined above. Such oxidation reaction is performed by the conventional method known for the conversion of alcohols to aldehydes or carboxylic acids. Thus, for instance, the oxidation methods using chromic anhydride-sulfuric acid, chromic anhydride-pyridine or the like are advantageous for the production of the carboxyl compounds, whereas the oxidation methods using activated manganese dioxide, N-chlorosuccinimide-dimethyl sulfide or -tetrahydrothiophene are suited for the production of the formyl compounds. The oxidation with chromic anhydride is preferably carried out in acetone or aqueous acetone within the temperature range of 0°–10° C. In the production of the formyl compounds, anhydrous chloroform or anhydrous methylene chloride is generally used as a solvent and, when activated manganese dioxide is used, the reaction can be carried out at −20° C. to room temperature.

Among the compounds (Ia), a compound of the formula:

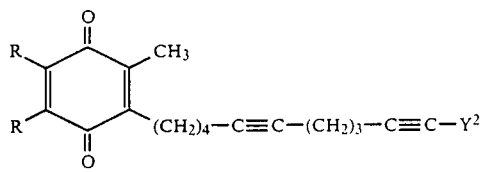

(Ia-B)

wherein $Y^2$ is carbamoyloxymethyl and R is as defined above, can also be produced by subjecting a compound of the formula (III) to carbamoylation. This reaction is generally carried out by reacting a compound (III) with trifluoroacetic acid and potassium cyanate in the absence or presence of a solvent such as methylene chloride, chloroform, benzene, etc. Potassium cyanate is usually used in an amount ranging from 1 to 2 moles per mole of compound (III). The reaction temperature is usually 10° to 40° C., and the reaction time is usually 1 to 5 hours.

Among the compounds (Ia), a compound of the formula:

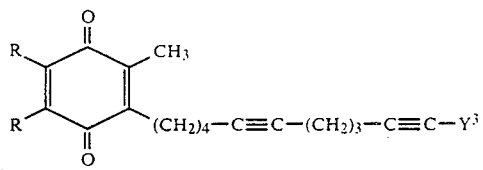

(Ia-C)

wherein $Y^3$ is alkoxycarbonyl having 2 to 5 carbon atoms and R is as defined above, can also be produced by esterifying a compound of the formula:

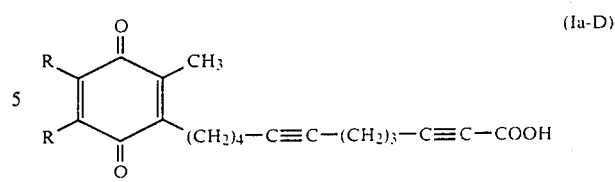

(Ia-D)

wherein R is as defined above. This reaction is carried out by reacting a compound (Ia-D) with an alcohol and thionylchloride. The alcohol includes methanol, ethanol, propanol, isopropanol, and benzyl alcohol. The alcohol is usually used in an amount ranging from 10 to 100 moles per mole of compound (Ia-D), and thionylchloride is usually used in an amount ranging from 10 to 20 moles per mole of compound (Ia-D). A compound (Ia-C) wherein $Y^3$ is methoxycarbonyl can also be produced by reacting a compound (Ia-D) with diazomethane. In this reaction diazomethane is usually used in an amount ranging from 1 to 2 moles per mole of compound (Ia-D). Each of the esterification reactions is usually carried out at a temperature ranging from 0° C. to room temperature for 1 to 24 hours.

Among the compounds (Ia), a compound of the formula:

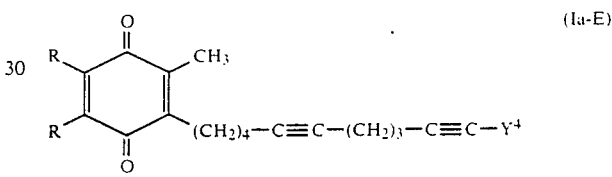

(Ia-E)

wherein $Y^4$ is carbamoyl or a mono- or di-alkylcarbamoyl whose alkyl moiety has 1 to 4 carbon atoms and R is as defined above, can also be produced by subjecting a compound of the formula (Ia-D) to amidation. This reaction is usually carried out by reacting a compound (Ia-D) with cyclohexylcarbodiimide (DCC) or with an active ester which is usually used in the synthesis of peptides. The amount of DCC or the active ester to be used is usually in the range of 1 to 1.5 moles per mole of compound (Ia-D). The reaction temperature is usually in the range of from −10° C. to room temperature and the reaction time is usually 1 to 10 hours.

A hydroquinone compound of the formula (Ib) can be produced by reducing a compound of the formula (Ia). This reaction is usually carried out in a solvent such as ether, dioxane, methanol, ethanol, acetonitrile, or a mixture of water and one of these solvents. In this reaction, a relatively mild reducing agent such as sodium hydrosulfite or sodium borohydride is used. The amount of the reducing agent to be used is in the range of from 2 to 5 moles per mole of compound (Ia). The reaction temperature is in the range of from 10° C. to room temperature. Further, this reaction is carried out by catalytic reduction with the use of palladium carbon or platinum oxide. In this case, the completion of the reaction is indicated by the change of yellow or orange yellow to colorless, the color change occurring when compound (Ia) absorbs one equivalent of hydrogen.

The quinone compounds (Ia) of the invention and the hydroquinone compounds (Ib) of the invention should be considered as pharmacologically equivalent since the former and the latter are interconvertible to each other under physiological conditions. From the chemical viewpoint, the hydroquinone compounds (Ib) are generally susceptible to oxidation, and therefore they should preferably be handled in the form of quinone compounds (Ia). The hydroquinone compounds (Ib) can be converted to stable forms, such as the above-mentioned compounds (II), by introducing a protective group into the hydroxyl groups thereof by the per se known methods (e.g. etherification, benzylation, acylation).

The thus-produced quinone compounds (Ia) and hydroquinone compounds (Ib) corresponding thereto can be isolated by the per se known separation and purification techniques (e.g. chromatography, distillation, crystallization).

The compounds (Ia) and (Ib) of the present invention exert significant influence on the metabolism of polyunsaturated fatty acids (PUFAs), such as linoleic acid, linolenic acid, dihomo-γ-linolenic acid, arachidonic acid and eicosapentaenoic acid, especially in the lipoxygenase system and in the cyclooxygenase system. Thus, for instance, they inhibit the production of SRS-A (slow reacting substance of anaphylaxis), which is known to play a pathophysiological role in immediate hypersensitivity reactions, and at the same time inhibit the formation of 5-hydroperoxyeicosatetraenoic acid (5-HPETE) and 5-hydroxyeicosatetraenoic acid (5-HETE).

The precursor of 5-HPETE is arachidonic acid, and 5-HPETE is one of hydro peroxyfatty acids produced by lipoxygenase in human leukocytes, rat mast cells and so on and also in an important intermediate of SRS-A (leukotrienes) [Proc. Natl. Acad. Sci., U.S.A. vol. 76, page 4275 (1979)].

A characteristic feature of the compounds of the present invention is that they hardly undergo reduction in the number of side chain carbon atoms in the metabolic systems of living bodies and therefore can remain in living bodies for a prolonged period of time, so that effective drug concentrations in plasma can be retained for a long time.

Owing to their PUFA metabolism-improving action, especially the hydro peroxyfatty acid production-inhibiting (antioxidant) action or SRS-A production-inhibiting action, the compounds (Ia) and (Ib) of the present invention exhibit a diversity of physiological actions mammals, such as antiasthmatic, antiallergic, hypertensive, arteriosclerosis-ameliorating, atherosclerosis-ameliorating, platelet aggregation tendency-ameliorating, renal, cerebral and cardiac vascular system-improving, anti-ulcer, diuretic, immunoregulatory and bacterial infection-preventing actions. They are thus widely useful as drugs, such as antiasthmatic, antiallergic, antihypertensive, antiulcer, diuretic, antithrombotic, cerebral circulation-improving, coronary vessel-improving, immunoregulatory, bacterial infection prevention-promoting and prostaglandin-thromboxane metabolism-improving agents, for the treatment or prevention of bronchial asthma, allergic diseases, hypertension, cerebral thrombosis, ischemic myocardial infarction, coronary disorders, atherosclerosis, immunodeficiency and prostaglandin and thromoxane biosynthesis-regulating mechanism disorder, among others.

The compounds of the present invention have low toxicity and can be safely administered orally or parenterally either per se or in the form of pharmaceutical preparations [e.g. tablets, capsules (inclusive of soft capsules and microcapsules), solutions, injections, suppositories] prepared by mixing with per se known pharmaceutically acceptable carriers, excipients, etc. The dose may vary depending on the target of treatment, route of administration, symptom, and other factors. Where the compounds are orally administered, for instance, to human adults for the treatment of hypertension or bronchial asthma, it is advisable to administer them generally at a single dose of about 0.2 to 25 mg/kg body weight, preferably about 0.5 to 10 mg/kg body weight, once to about three times per day.

The starting compounds (II) or (III) for the method of production according to the invention are producible, for example, by the methods described in Japanese Patent Application laid open under No. 56-154433 (Kokai) and Japanese Patent Application laid open under No. 57-109739 or modifications thereof.

The following examples and experiments illustrate the present invention in more detail but are by no means limitative of the scope of the invention.

EXAMPLE 1

Jones reagent (60 ml) was added dropwise to an ice-cooled and stirred solution of 2.61 g of the alcohol (III) (R=CH$_3$) in 40 ml of acetone over 15 minutes. After the addition, the ice bath was removed, and the mixture was stirred at room temperature for 45 minutes. Water (30 ml) was added to the reaction mixture, and then the acetone was distilled off under reduced pressure. Ethyl acetate (50 ml) was added to the residue for extraction, the organic layer was washed with water and then with aqueous sodium chloride, and then 50 ml of an aqueous solution of sodium hydrogen carbonate was added to the organic layer for transfer of the product into the aqueous layer. The aqueous layer was separated, made acidic with dilute hydrochloric acid, and extracted with 60 ml of isopropyl ether. The isopropyl ether layer was washed with water and aqueous sodium chloride, and dried over magnesium sulfate. The isopropyl ether was then distilled off under reduced pressure, and the residue was subjected to silica gel column chromatography using isopropyl ether as eluant to give 2.28 g (84%) of the desired carboxylic acid compound (Ia-3 in Table 1, R=CH$_3$, Y=COOH).

EXAMPLE 2

To a solution of 0.33 g of the alcohol (III) (R=CH$_3$) in 20 ml of dichloromethane, there was added 2.0 g of active manganese dioxide, and the mixture was stirred at room temperature for an hour. After completion of the reaction, the manganese dioxide was filtered off and the dichloromethane was distilled off under reduced pressure. The residue was subjected to silica gel column chromatography (eluant: isopropyl ether-hexane) to give 0.29 g (90%) of the desired aldehyde compound (Ia-1 in Table 1, R=CH$_3$, Y=CHO).

EXAMPLE 3

Toluene (30 ml) was added to a mixture of 3.26 g (10 millimoles) of the alcohol (III) (R=CH$_3$) and 2.43 g (30 millimoles) of potassium cyanate, and the mixture was stirred at room temperature. Thereto was added dropwise 3.76 g (33 millimoles) of trifluoroacetic acid over 10 minutes. After the addition, the mixture was stirred at 35°-40° C. for 4 hours. Isopropyl ether (60 ml) and water (50 ml) were added to the reaction mixture. The insoluble matter was filtered off through Celite, and the organic layer was separated, washed with aqueous sodium chloride and dried over magnesium sulfate. The solvent was then distilled off. The residue was purified by silica gel column chromatography [eluant: isopropyl ether-ethyl acetate (4:1)] to give the carbamoyl ester compound (Ia-7). Yield 2.57 g (70%, recrystallized from isopropyl ether).

Another carbamoyl ester compound (Ia-8) was produced from the alcohol (III) (R=OCH$_3$) in the same manner as above.

EXAMPLE 4

To a solution of 0.30 g of the carboxylic acid Ia-3 (R=CH$_3$, Y=COOH) as obtained in Example 1 in 5 ml of ethyl ether, there was added a solution of diazomethane in ethyl ether until the starting carboxylic acid (Ia-3) was no longer detected. After completion of the reaction, the ethyl ether was distilled off, and the residue was purified by silica gel column chromatography using isopropyl ether-hexane as eluant to give 0.30 g (96%) of the desired carboxylic acid methyl ester (Ia-5, R=CH$_3$, Y=CO$_2$CH$_3$).

EXAMPLE 5

To a solution of 300 mg of the carboxylic acid compound (Ia-3) as obtained in Example 1 in 5 ml of methylene chloride, there were added 150 mg of 2-thiazoline-2-thiol and 200 mg of dicyclohexylcarbodiimide, and the mixture was stirred at room temperature for 20 minutes. To this mixture was added 60 mg of isopropylamine, and the resulting mixture was stirred under the same reaction conditions for 2 hours. Thereafter, the crystalline precipitate was filtered off, the filtrate was washed with water, dried over magnesium sulfate and concentrated, and the residue was subjected to silica gel column chromatography using isopropyl ether-ethyl acetate as eluant. Fractions containing the desired product were gathered and concentrated to give the desired quinone compound (Ia-10). The physical properties and other characteristics of said compound are shown in Table 1.

Following the same procedure but using ammonia in place of isopropylamine, there was obtained another quinone compound (Ia-9).

The compounds obtained by the same procedure as in any of the examples mentioned above or a modification thereof are listed in Table 1 (A, B) together with their physical properties.

TABLE 1

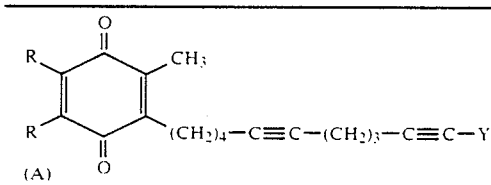

(Ia)

| (A) | | | | |
|---|---|---|---|---|
| Compound No | R | Y | Molecular formula (melting point) | Elemental analysis Found (calculated) C H |
| Ia-1 | CH$_3$ | CHO | C$_{21}$H$_{24}$O$_3$ | 77.46 (77.75) 7.57 (7.46) |
| Ia-2 | OCH$_3$ | CHO | C$_{21}$H$_{24}$O$_5$ | 70.64 (70.77) 6.52 (6.79) |
| Ia-3 | CH$_3$ | COOH | C$_{21}$H$_{24}$O$_4$ | 74.18 (74.09) 7.24 (7.11) |
| Ia-4 | OCH$_3$ | COOH | C$_{21}$H$_{24}$O$_6$ | 67.82 (67.73) 6.47 (6.50) |
| Ia-5 | CH$_3$ | COOCH$_3$ | C$_{22}$H$_{26}$O$_4$ | 74.73 (74.55) 7.43 (7.39) |
| Ia-6 | OCH$_3$ | COOCH$_3$ | C$_{22}$H$_{26}$O$_6$ | 68.27 6.88 |
| Ia-7 | CH$_3$ | CH$_2$OCONH$_2$ | C$_{22}$H$_{27}$NO$_4$ (56~57° C.) | (68.38) (6.78) 71.65 7.55 (71.52) (7.37) |
| Ia-8 | OCH$_3$ | CH$_2$OCONH$_2$ | C$_{22}$H$_{27}$NO$_6$ (44~45° C.) | 66.06 6.56 (65.82) (6.78) |
| Ia-9 | CH$_3$ | CONH$_2$ | C$_{21}$H$_{25}$NO$_3$ | 74.08 7.64 (74.31) (7.42) |
| Ia-10 | CH$_3$ | CONHCH(CH$_3$)$_2$ | C$_{24}$H$_{31}$NO$_3$ | 75.29 8.04 (75.55) (8.19) |

| (B) | |
|---|---|
| Compound No. | Nuclear magnetic resonance spectra (δ value, p.p.m.) (TMS Internal standard) |
| Ia-1 | 1.4~1.6 (4H), 1.75 (2H), 2.01 (6H), 2.03 (3H), 2.1~2.3 (4H), 2.3~2.5 (2H), 2.54 (2H), 9.16 (1H) |
| Ia-2 | 1.4~1.6 (4H), 1.75 (2H), 2.02 (3H), 2.1~2.3 (4H), 2.3~2.5 (2H), 2.53 (2H), 3.98 (6H), 9.16 (1H) |
| Ia-3 | 1.4~1.6 (4H), 1.78 (2H), 2.01 (6H), 2.03 (3H), 2.1~2.3 (4H), 2.3~2.5 (2H), 2.47 (2H), 7.41 (1H) |
| Ia-4 | 1.4~1.9 (6H), 2.03 (3H), 2.1~2.6 (8H), 3.99 (6H), 7.10 (1H) |
| Ia-5 | 1.4~1.6 (4H), 1.77 (2H), 2.00 (6H), 2.02 (3H), 2.1~2.3 (4H), 2.3~2.5 (2H), 2.44 (2H), 3.74 (3H) |
| Ia-6 | 1.4~1.6 (4H), 1.76 (2H), 2.01 (3H), 2.1~2.3 (4H), 2.3~2.5 (2H), 2.44 (2H), 3.73 (3H), 3.97 (6H) |
| Ia-7 | 1.4~1.9 (6H), 2.00 (6H), 2.04 (3H), 2.1~2.4 (6H), 2.48 (2H), 4.65 (2H), 4.85 (2H) |
| Ia-8 | 1.4~1.9 (6H), 2.03 (3H), 2.1~2.6 (8H), 4.00 (6H), 4.66 (2H), 4.91 (2H) |
| Ia-9 | 1.4~1.6 (4H), 1.78 (2H), 2.01 (6H), 2.03 (3H), 2.1~2.3 (4H), 2.3~2.5 (2H), 2.48 (2H), 5.80 (2H) |
| Ia-10 | 1.13 (6H), 1.4~1.6 (4H), 1.72 (2H), 2.02 (6H), 2.04 (3H), 2.1~2.3 (4 H), 2.3~2.5 (2H), 2.48 (2H), 4.01 (1H), 5.41 (1H) |

EXAMPLE 6

To a solution of 0.34 g (1.0 mmole) of 2,3,5-trimethyl-6-(11-carboxyundeca-5,10-diynyl)-1,4-benzoquinone (Ia: R=CH$_3$, Y=COOH) in ether (5 ml) was added a solution of sodium hydrosulfite (0.35 g, 2.0 mmole) in water (4 ml). The mixture was stirred at room temperature for 1 hour. The ether layer was taken out and washed with aqueous solution saturated with sodium chloride. The ether solution was dried over magnesium sulfate, and solvent was evaporated to give 0.28 g of 2,3,5-trimethyl-6-(11-carboxyundeca-5,10-diynyl)-1,4-hydroquinone (Ib: R=CH$_3$, Y=COOH) as white crystals. m.p. 87°–89° C.

EXAMPLE 7

By a similar manner to Example 6, 0.26 g of white crystals of 2-(12-carbamoyloxydodeca-5,10-diynyl)-3,5,6-trimethyl-1,4-hydroquinone (Ib: R=CH$_3$, Y=CH$_2$OCONH$_2$) melting at 90°-92° C. were obtained from 0.33 g (1.0 mmole) of 2-(12-carbamoyloxydodeca-5,10-diynyl)-3,5,6-trimethyl-1,4-benzoquinone (Ia: R=CH$_3$, Y=CH$_2$OCONH$_2$).

EXAMPLE 8

By a similar manner to Example 1, 3.56 g (10 mmoles) of 1-(12-hydroxydodeca-5,10-diynyl)-2,5-dimethoxy-3,4,6-trimethylbenzene (II: R=R$^1$=CH$_3$, Y=CH$_2$OH) was oxidized with chromic acid-sulfuric acid, whereby 12.62 g of 1,4-dimethoxy-2,3,5-trimethyl-6-(11-carboxyundeca-5,10-diynyl)benzene was obtained as an oily substance. In a mixed solvent of acetonitrile (40 ml) and water (20 ml) were dissolved 2.60 g (7.0 mmole) of the compound obtained above and 3.80 g (7.0×3 mmoles) of 2,6-dicarboxypyridine N-oxide, and the solution was stirred under cooling with ice. An ice-cooled solution of ceric ammonium nitrate (11.4 g, 7.0×3 mmoles) in 50% aqueous acetonitrile (60 ml) was added dropwise to the above solution over a period of 30 minutes, followed by stirring under the same conditions for 30 minutes and at room temperature for 30 minutes. After the completion of the reaction, insolubles were filtered out, and the acetonitrile was distilled off under reduced pressure. To the residue were added isopropyl ether (100 ml) and water (20 ml) for extraction, and the organic layer was washed with saturated sodium bicarbonate and aqueous sodium chloride, successively and dried (over MgSO$_4$), followed by distilling off the organic solvent under reduced pressure. The residue was chromatographed on a column of silica gel developing with isopropyl ether:ethyl acetate (98:2 to 95:5) to give 2.10 g of 2,3,5-trimethyl-6-(11-carboxyundeca-5,10-diynyl)-1,4-benzoquinone. m.p. 49°-51° C.

EXAMPLE 9

To a methanolic solution (5 ml) of 300 mg of 2-(12-carbamoyloxydodeca-5,10-diynyl)-3,5,6-trimethyl-1,4-bis-(2-tetrahydropyranyloxy)benzene was added 0.05 g of camphor sulfonic acid, and the mixture was kept standing in nitrogen atmosphere for 3 hours. After the completion of the reaction, the solvent was evaporated, and ether was added to the residue. The ether layer was washed with water and dried over magnesium sulfate. The solvent was evaporated and the residue was recrystallized from isopropyl ether to give 105 mg of 2-(12-carbamoyloxydodeca-5,10-diynyl)-3,5,6-trimethyl-1,4-hydroquinone. m.p.: 90°-92° C.

REFERENCE EXAMPLE 1

In anhydrous methylene chloride (5 ml) was dissolved 2-(12-carbamoyloxydodeca-5,10-diynyl)-3,5,6-trimethyl-1,4-hydroquinone (186 mg, 0.5 mmole). To the solution were added dihydropyran (100 mg) and camphor sulfuric acid (5 mg). The mixture was kept standing at room temperature for 4 hours. The reaction mixture was concentrated under reduced pressure to about 1 ml. The residue was subjected to column chromatography on silica gel. Development with the use of isopropyl ether gives 2-(12-carbamoyloxydodeca-5,10-diynyl)-3,5,6-trimethyl-1,4-bis-(2-tetrahydropyranyloxy)benzene (250 mg) as an oily substance.

EXAMPLE 10

By a similar manner to Example 8, 2-(12-carbamoyloxydodeca-5,10-diynyl)-1,4-dimethoxy-3,5,6-trimethylbenzene (200 mg) was subjected to oxidative demethylation. The reaction mixture was subjected to column chromatography on silica gel. Recrystallization from isopropyl ether gave 2-(12-carbamoyloxydodeca-5,10-diynyl)-3,5,6-trimethyl-1,4-benzoquinone (120 mg). m.p. 56°-57° C.

EXAMPLE 11

Examples of Pharmaceutical Composition

| (A) Capsule | | | |
|---|---|---|---|
| (1) | Compound (Ia-3) | | 50 mg |
| (2) | Cellulose fine powder | | 30 mg |
| (3) | Lactose | | 37 mg |
| (4) | Magnesium stearate | | 3 mg |
| | | Total | 120 mg |

All the materials were mixed and filled into a gelatin capsule.

| (B) Soft Capsule | | | |
|---|---|---|---|
| (1) | Compound (Ia-7) | | 50 mg |
| (2) | Corn starch oil | | 100 mg |
| | | Total | 150 mg |

A mixed solution of (1) and (2) was prepared and filled into a soft capsule by a conventional manner.

| (C) Tablet | | | |
|---|---|---|---|
| (1) | Compound (Ia-3) | | 50 mg |
| (2) | Lactose | | 34 mg |
| (3) | Corn starch | | 10.6 mg |
| (4) | Corn starch (gelatinized) | | 5 mg |
| (5) | Magnesium stearate | | 0.4 mg |
| (6) | Calcium carboxymethyl cellulose | | 20 mg |
| | | Total | 120 mg |

All the materials were mixed and compressed by a tabletting machine to prepare a tablet in accordance with a conventional manner.

EXPERIMENT 1

Inhibitory effect on generation and release of SRS-A

The compounds obtained in accordance with the invention were assayed for the inhibitory effect on the generation of SRS-A by the method of Orange and Moore [J. Immunol., vol. 116, page 392 (1976)]. Thus, the test compound and antigen (egg white albumin) were simultaneously added to the lung fragments from guinea pigs (Hartley strain, male and female, weighing 300–350 g) sensitized with egg white albumin as the antigen. The quantity of SRS-A generated and released on that occasion was determined by the method of Brocklehurst [J. Physiol., vol. 151, pages 416–435 (1960)]. As is seen in Table 2, the compounds of the invention strongly inhibited the generation and release of SRS-A at low concentrations.

| Compound No. | Number of experiments | Concentration of test compound | Inhibitory effect on SRS-A generation and release (%) |
| --- | --- | --- | --- |
| Ia-1 | 3 | $10^{-6}$M | 59 ± 15 |
| Ia-2 | 3 | $10^{-6}$M | 66 ± 6 |
| Ia-3 | 3 | $10^{-6}$M | 58 ± 6 |
| Ia-4 | 3 | $10^{-6}$M | 61 ± 8 |

EXPERIMENT 2

Inhibition of 5-lipoxygenase products in RBL-1 cells

RBL-1 cells (rat basophilic leukemia cells) ($10^7$ cells) were suspended in 0.5 ml of MCM (mast cell medium), the test solution (composed of 0.5 ml MCM, 50 μg arachidonic acid, 10 μg A-23187 and $10^{-6}$M or $10^{-5}$M quinone compound) was added, and the mixture was incubated at 37° C. for 20 minutes. Thereafter, 4 ml of ethanol and 1,4-dimethoxy-2-methyl-3-(3-methoxypropyl)naphthalene (internal standard) were added, and the mixture was shaken well, then allowed to stand at room temperature for 10 minutes, and centrifuged at 2,000 revolutions per minute for 10 minutes. The supernatant was collected and concentrated to about 200 μl under reduced pressure. A mixed solvent for high performance liquid chromatography [CH$_3$CN (1500)-CH$_3$OH (500)-water (1100)-acetic acid (2), adjusted to pH 5.6 with aqueous ammonia] was added to the concentrate to make up to 1 ml. A 200-μl portion of this solution was subjected to high performance liquid chromatography for assaying 5-HETE (5-hydroxyeicosatetraenoic acid).

The percentage of inhibition of 5-HETE production (IE) is expressed by (1-b/a)×100, where a is the peak height or area corrected relative to the internal standard peak for the quinone compound-free (control) test solution and b is the peak height or area corrected in relation to the internal standard peak for the quinone compound-containing test solution.

TABLE 3

| Compound No. | Percent inhibition of generation and release of 5-HETE Concentration of test compound | |
| --- | --- | --- |
|  | $10^{-5}$M | $10^{-6}$M |
| Ia-1 | 83.5 | 71.6 |
| Ia-2 | 84.3 | 72.3 |
| Ia-3 | 86.7 | 75.3 |
| Ia-4 | 85.4 | 70.6 |
| ETYA* | 39.4 | 35.9 |

*Control compound: 5,8,11,14-eicosatetraynoic acid

What is claimed is:

1. A compound of the formula:

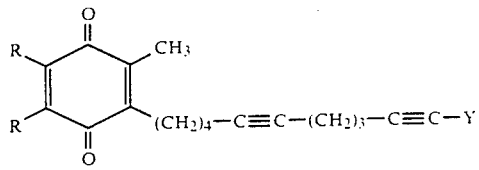

wherein
R is methyl or methoxy and
Y is formyl, carboxyl, an alkoxycarbonyl having 2 to 5 carbon atoms, carbamoyl, a mono- or dialkylcarbamoyl whose alkyl moiety has 1 to 4 carbon atoms, or carbamoyloxymethyl, or its hydroquinone-form compound, or a pharmaceutically acceptable salt thereof.

2. A compound as claimed in claim 1, wherein the compound is in the quinone form.

3. A compound as claimed in claim 1, wherein Y is carboxyl.

4. A compound as claimed in claim 1, wherein Y is carbamoyloxymethyl.

5. A compound as claimed in claim 1, wherein the compound is 2,3,5-trimethyl-6-(11-carboxyundeca-5,10-diynyl)-1,4-benzoquinone.

6. A compound as claimed in claim 1, wherein the compound is 2,3-dimethoxy-5-methyl-6-(11-carboxyundeca-5,10-diynyl)-1,4-benzoquinone.

7. A compound as claimed in claim 1, wherein the compound is 2-(12-carbamoyloxydodeca-5,10-diynyl)-3,5,6-trimethyl-1,4-benzoquinone.

8. A compound as claimed in claim 1, wherein the compound is 2-(12-carbamoyloxydodeca-5,10-diynyl)-5,6-dimethoxy-3-methyl-1,4-benzoquinone.

9. A pharmaceutical composition suitable for suppressing the generation and release of SRS-A, which comprises as an active ingredient, an effective amount of a compound of the formula:

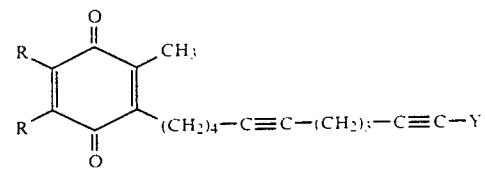

wherein
R is methyl or methoxy and
Y is formyl, carboxyl, an alkoxycarbonyl having 2 to 5 carbon atoms, carbamoyl, a mono- or dialkylcarbamoyl whose alkyl moiety has 1 to 4 carbon atoms, or carbamoyloxymethyl, or its hydroquinone-form compound, or a pharmaceutically acceptable salt thereof, and a pharmaceutically acceptable carrier or excipient therefor.

* * * * *